United States Patent
Senthilkumar et al.

(10) Patent No.: US 8,212,024 B2
(45) Date of Patent: Jul. 3, 2012

(54) CRYSTALLINE SODIUM SALT OF CEPHALOSPORIN ANTIBIOTIC

(75) Inventors: Udayampalayam Palanisamy Senthilkumar, Chennai (IN); Kanagaraj Suresh Kumar, Chennai (IN); Singaravel Mohan, Chennai (IN); Lakshminarayanan Arunkumar, Chennai (IN); Bakthavachalam Ananthan, Chennai (IN)

(73) Assignee: Orchid Chemicals & Pharmaceuticals Ltd., Chennai (IN)

( * ) Notice: Subject to any disclaimer, the term of this patent is extended or adjusted under 35 U.S.C. 154(b) by 645 days.

(21) Appl. No.: 12/089,821

(22) PCT Filed: Oct. 12, 2006

(86) PCT No.: PCT/IB2006/002842
§ 371 (c)(1),
(2), (4) Date: Apr. 10, 2008

(87) PCT Pub. No.: WO2007/042917
PCT Pub. Date: Apr. 19, 2007

(65) Prior Publication Data
US 2008/0221076 A1    Sep. 11, 2008

(30) Foreign Application Priority Data

Oct. 12, 2005  (IN) ............. 1462/CHE/2005
Nov. 18, 2005  (IN) ............. 1680/CHE/2005

(51) Int. Cl.
*C07D 501/36* (2006.01)
*A61K 31/546* (2006.01)

(52) U.S. Cl. .................................... 540/227

(58) Field of Classification Search ............ None
See application file for complete search history.

(56) References Cited

U.S. PATENT DOCUMENTS

| | | | | |
|---|---|---|---|---|
| 6,458,949 | B1 * | 10/2002 | Handa et al. | 540/226 |
| 6,555,680 | B1 * | 4/2003 | Deshpande et al. | 540/227 |
| 6,803,461 | B2 * | 10/2004 | Deshpande et al. | 540/226 |
| 7,071,329 | B2 * | 7/2006 | Monguzzi et al. | 540/226 |
| 7,345,169 | B2 * | 3/2008 | Senthilkumar et al. | 544/227 |
| 7,511,135 | B2 * | 3/2009 | Tyagi et al. | 540/227 |
| 2002/0028931 | A1 | 3/2002 | Dandala et al. | |
| 2002/0082248 | A1 * | 6/2002 | Berger et al. | 514/206 |
| 2003/0065168 | A1 | 4/2003 | Deshpande et al. | |
| 2004/0132996 | A1 * | 7/2004 | Tyagi et al. | 540/227 |
| 2005/0119244 | A1 * | 6/2005 | Monguzzi et al. | 514/202 |
| 2006/0094872 | A1 * | 5/2006 | Senthilkumar et al. | 540/217 |
| 2006/0135761 | A1 * | 6/2006 | Datta et al. | 540/222 |
| 2008/0207912 | A1 * | 8/2008 | Tyagi et al. | 548/195 |

OTHER PUBLICATIONS

International Search Report (PCT/IB2006/002842) mailed Dec. 14, 2006.

* cited by examiner

*Primary Examiner* — Mark Berch
(74) *Attorney, Agent, or Firm* — Oliff & Berridge, PLC

(57) ABSTRACT

The present invention relates to novel polymorph of Ceftiofur sodium as a crystalline product. The present invention also provides a process for the preparation of crystalline Ceftiofur sodium of formula (I).

(I)

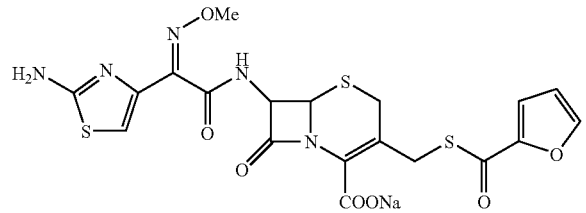

8 Claims, 1 Drawing Sheet

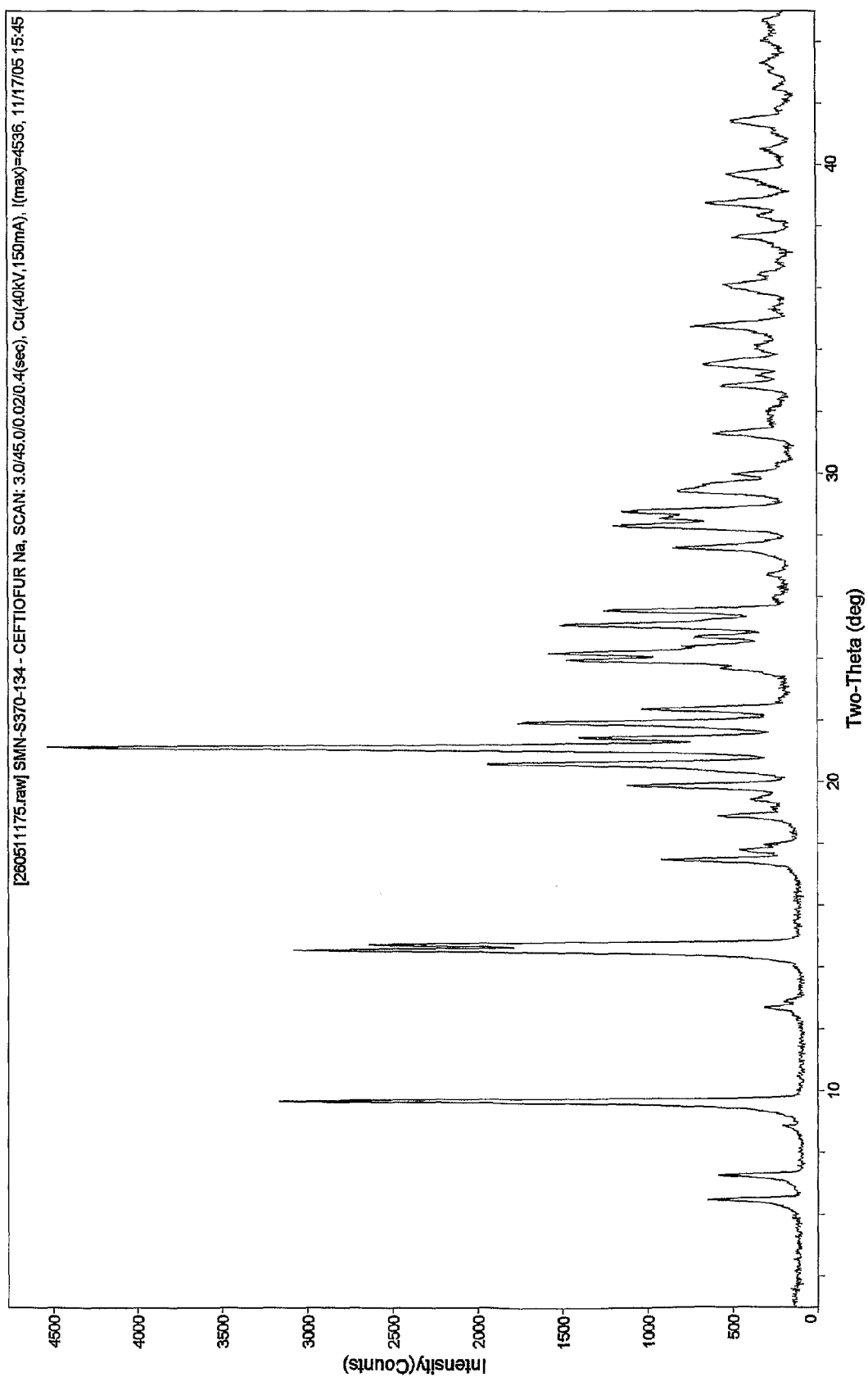

CRYSTALLINE SODIUM SALT OF CEPHALOSPORIN ANTIBIOTIC

CROSS-REFERENCE TO RELATED APPLICATIONS

This application is the U.S. National Stage of International Application No. PCT/IB2006/002842, filed Oct. 12, 2006, which claims benefit of Application No. 1462/CHE/2005 and Application No. 1680/CHE/2005, filed Oct. 12, 2005, and Nov. 18, 2005, respectively.

FIELD OF THE INVENTION

The present invention relates to novel polymorph of Ceftiofur sodium as a crystalline product and relates to a process for the preparation of Ceftiofur sodium as a crystalline product. The present invention further provides a process for crystallizing Ceftiofur sodium directly from the reaction mass.

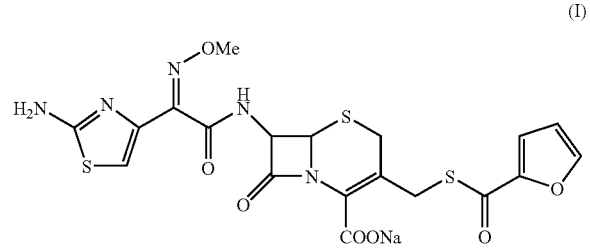

(I)

BACKGROUND OF THE INVENTION

Ceftiofur, a semisynthetic cephalosporin, is a broad-spectrum antibiotic against both Gram-positive and Gram-negative bacteria including beta-lactamase-producing bacterial strains and anaerobes. Its antibacterial activity results from the inhibition of mucopeptide synthesis in the cell wall in a similar fashion to other cephalosporins. Ceftiofur is used in the treatment of respiratory infections in cattle and pigs. The chemical designation is 7-[[(2-amino-4-thiazolyl)(methoxyimino)acetyl]amino]-3-[[2-furanylcarbonyl)thio]methyl]-8-oxo-5-thia-1-azabicyclo[4.2.0]oct-2-ene-2-carboxylic acid. The sodium and hydrochloride salts are administered intramuscularly and intravenously.

Ceftiofur is first disclosed in U.S. Pat. No. 4,464,367, which also discloses a process for preparing Ceftiofur and its sodium salt.

U.S. Pat. No. 4,902,683 claims crystalline hydrochloride salt of Ceftiofur. According to this patent the conventional free acid and its sodium salt are unstable and are obtained as amorphous nature.

U.S. Pat. No. 5,721,359 claims a crystalline Ceftiofur free acid and a process for the preparation of the same.

U.S. Pat. No. 4,937,330 claims a process for the preparation of Ceftiofur sodium, though this patent mentioned the Ceftiofur sodium obtained according to this patent as a crystal form, this patent does not provide the X-ray diffraction pattern of the said crystal. According to this patent Ceftiofur sodium salt as isolated from aqueous tetrahydrofuran as a unique solid phase characterized by birefringent lath- and rod-shaped particles. However the x-ray diffraction of this unique gave no diffraction pattern. Moreover further treatment with a dry organic solvent (e.g., acetone or ethanol) produces solvent-free amorphous Ceftiofur sodium upon drying.

Hence all the prior art literature reported so far provide amorphous Ceftiofur sodium, and, owing to the amorphous nature, the conventional Ceftiofur sodium is less stable. Further, owing to the amorphous nature, purification is very difficult, and hence not preferable in industrial point of view.

The amorphous form of Ceftiofur salts such as sodium salt and amine salt and ester forms of this cephalosporin antibiotic are somewhat unstable chemically and are difficult to purify, and are less desirable to work with in manufacturing pharmaceutical formulations containing them. This amorphous salts are difficult solids to isolate in pure form and handle in pharmaceutical manufacturing plants. Hence there is a need to prepare Ceftiofur Sodium in a crystalline form.

WO 02/42266 claims a process for the production of Ceftiofur sodium treating the Ceftiofur hydrochloride with sodium source, separating sodium chloride using appropriate membrane (reverse osmosis technique to remove sodium chloride), and isolating Ceftiofur sodium by lyophilization.

U.S. Pat. No. 6,458,949 discloses a process in which after completion of cyclization with thiourea in example 1, sodium chloride was added into reaction mass, the resultant by-phasic layer was separated, followed by addition of sodium 2-ethyl hexonate to yield Ceftiofur sodium.

U.S. Pat. No. 6,555,680 discloses a process in which Ceftiofur sodium was prepared from Ceftiofur amine salt, however the complexity associated with work up procedure makes this process unfavorable for plant point of view.

Conventional process reported for the preparation of Ceftiofur sodium involves dissolution of Ceftiofur acid in a solvent like acetone, methanol, THF, water or mixtures thereof using an organic amine followed by the addition of sodium salt of weak acid like sodium 2-ethyl hexonate or neutralizing the Ceftiofur hydro halide salt with sodium ion source followed by converting the acid into Ceftiofur sodium by using membrane filtration.

In our continued research we have identified a process for the preparation of Ceftiofur sodium as a crystalline product, the crystalline Ceftiofur sodium prepared according to our invention is novel and having good stability over conventional amorphous product. None of the prior art suggests or event motivates the present invention.

OBJECTIVES OF THE INVENTION

The primary objective of the invention is to provide a crystalline salt of Ceftiofur sodium of formula (I), which is having good stability than conventional amorphous Ceftiofur sodium.

Another objective of the present invention is to provide a pharmaceutical composition containing crystalline salt of Ceftiofur sodium.

Still another objective of the invention is to provide an improved process for the crystallization of Ceftiofur sodium of formula (I) with good purity directly from the reaction mixture.

Yet another objective of the present invention is to provide a commercial process for the direct isolation of Ceftiofur sodium without converting the Ceftiofur sodium into acid addition salt.

One more objective of the present invention is to provide a process for the preparation of Ceftiofur sodium that obviates the use of amine, sodium salt of weak acid like sodium 2-ethylhexonate and membrane filtration.

SUMMARY OF THE INVENTION

Accordingly, the present invention provides novel crystalline form of Ceftiofur sodium of formula (I)

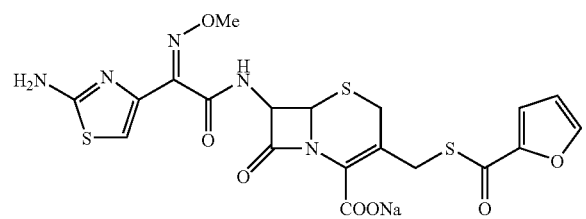

(I)

having substantially the same X-ray diffractogram as set out in FIG. 1.

The present invention also provides a process for the preparation of novel crystalline form of Ceftiofur sodium, which comprises the steps of:
i) dissolving Ceftiofur sodium in water,
ii) optionally adding an organic solvent,
iii) adding alkaline or alkaline earth metal salts selected from group comprising of sodium chloride, sodium bicarbonate, sodium sulphate, sodium bromide and potassium dihydrgen orthophospate and or mixture there of
iv) isolating Ceftiofur as crystalline product.

Another embodiment of the invention further relates to an improved process for the preparation of Ceftiofur sodium of formula (I)

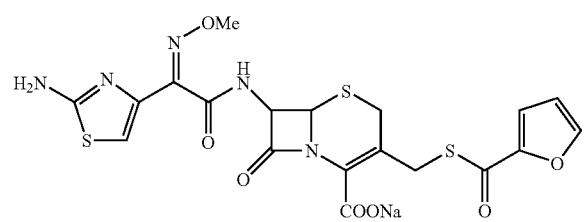

(I)

the said process comprising the steps of:
a) preparing Ceftiofur sodium in the presence or absence of water miscible organic solvent and water, in the presence of sodium ion source by acylating FURACA of formula (II),

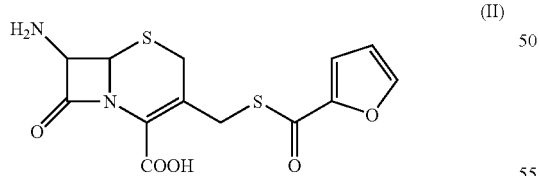

(II)

b) optionally removing the organic solvent,
c) optionally adding inorganic salts selected from group comprising of sodium chloride, sodium sulphate, or sodium bromide, and
d) isolating Ceftiofur sodium of formula (I) by filtration.

DESCRIPTION OF FIGURES

FIG. 1: Powder XRD pattern of crystalline form of Ceftiofur sodium of formula (I) analyzed by X-Ray Powder Diffractometer of following features:

| Make | RIGAKU |
|---|---|
| Model | D/Max 2500 PC |
| Data handling system | JADE Version 6.5.19 |
| ANODE | COPPER |
| RADIATION | Cu K alpha-1 |
| WAVELENGTH | 1.54056 A° |
| CURRENT & VOLTAGE | 40 Kv & 150 mA |

DETAILED DESCRIPTION OF THE INVENTION

In an embodiment of the present invention, novel crystalline form of Ceftiofur sodium of the formula (I) is characterized by X-ray powder diffraction with data given in the following table:

| 2-Theta | I % |
|---|---|
| 6.481 | 11.4 |
| 7.278 | 10.8 |
| 8.838 | 1.6 |
| 9.68 | 71.4 |
| 12.699 | 4.9 |
| 12.899 | 2.1 |
| 14.559 | 69.5 |
| 14.738 | 59.3 |
| 17.48 | 18.6 |
| 17.762 | 7.7 |
| 17.96 | 3.8 |
| 18.899 | 8.7 |
| 19.421 | 3.4 |
| 19.879 | 20.7 |
| 20.58 | 40.5 |
| 21.139 | 100 |
| 21.42 | 23.8 |
| 21.919 | 34.9 |
| 22.36 | 17.5 |
| 23.681 | 7.8 |
| 23.94 | 27 |
| 24.16 | 28.7 |
| 24.702 | 7 |
| 25.08 | 27.6 |
| 25.559 | 23.5 |
| 25.979 | 1.4 |
| 26.704 | 2.4 |
| 27.599 | 14.9 |
| 28.3 | 22.9 |
| 28.541 | 15.8 |
| 28.76 | 21 |
| 29.44 | 14.4 |
| 29.98 | 6.8 |
| 31.281 | 10.1 |
| 31.979 | 2.6 |
| 32.839 | 8.3 |
| 33.161 | 2.1 |
| 33.521 | 9.3 |
| 34.122 | 2.2 |
| 34.78 | 11 |
| 35.359 | 1.2 |
| 36.1 | 7.7 |
| 36.441 | 2.9 |
| 36.919 | 0.9 |
| 37.641 | 7 |
| 38.34 | 3.3 |
| 38.76 | 10.6 |
| 39.699 | 7.3 |
| 40.52 | 2.6 |
| 41.06 | 1.9 |
| 41.42 | 7.9 |
| 41.822 | 2 |
| 42.479 | 1.8 |
| 43.04 | 2.1 |
| 43.32 | 2.5 |
| 44.041 | 2.1 |
| 44.7 | 2.2 |

In another embodiment of the present invention, novel crystalline form of Ceftiofur sodium of the formula (I) having an X-ray diffraction pattern which comprises the following characteristic peaks (±0.2θ): 9.68; 14.56, 14.74, 17.48, 19.88, 20.58, 21.14, 21.42, 21.92, 22.36, 23.94, 24.16, 25.08, 25.56, 28.30, 28.54, 28.76 in 2θ. Further the novel Ceftiofur crystalline sodium according to this invention having moisture content in the range of 7.0 to 11%.

In an embodiment of the present invention, the organic solvent used in step (ii) is selected from THF, acetone, ethyl acetate, butyl acetate, ethyl methyl ketone, diglyme, butanone, dioxane, DMF and the like.

In one more embodiment of the present invention, the crystalline Ceftiofur sodium of Formula 1 herein are useful as the active antibiotic drug compound in pharmaceutical dosage forms which will permit and provide higher bulk density forms of Ceftiofur.

Crystalline materials are preferred in most pharmaceutical applications since crystalline forms have better flow properties, and are thermodynamically more stable than amorphous forms of the same substance. This thermodynamic stability is reflected in the lower solubility and improved physical stability of the crystalline form. The regular packing of the molecules in the crystalline solid denies the incorporation of chemical impurities. Hence crystalline materials generally possess higher chemical purity than their amorphous counterparts.

The following Table provides a comparison of physical characteristics of amorphous and crystalline Ceftiofur Sodium. From this table it is evident that the crystalline Ceftiofur Sodium has better physical characteristics than amorphous material.

TABLE 1

Comparison between Amorphous and Crystalline Ceftiofur sodium

| No | Test | Amorphous | Crystalline |
|---|---|---|---|
| 1 | Description | Pale yellow to pale brown powder | Almost white to white sample |
| 2 | Tapped Bulk density | 0.5 g/ml | 0.8 g/ml |
| 3 | Reconstituted solution color | Pale Brown | Colorless to pale yellow |
| 4 | Total Related substances | 1.55% | 0.15% |

The following Tables (Table 2 & 3) provide stability data of crystalline Ceftiofur Sodium prepared according to this invention. From this it table it is evident that the crystalline Ceftiofur Sodium prepared according this invention is a very stable and a highly pure material, which is clearly indicated by total RS (Related substances) analysis & the stability data.

TABLE 2

Stability at 40 ± 2° C. & 75 ± 5% RH

| Assay | | | Total RS | | |
|---|---|---|---|---|---|
| Int. | 15 D | 2 M | Int | 15 D | 2 M |
| 101.25 | 100.64 | 100.61 | 0.61 | 0.78 | 0.93 |

Int: Initial,
15 D: 15 days;
2 M: 2 month

TABLE 3

Stability at 25 ± 2° C. & 60 ± 5% RH

| Assay | | | Total RS | | |
|---|---|---|---|---|---|
| Int. | 1 M | 2 M | Int | 1 M | 2 M |
| 101.25 | 101.18 | 100.31 | 0.61 | 0.75 | 0.78 |

Int: Initial,
M: 1 month;
2 M: 2 month;

Because of the good stability and purity of Crystalline Ceftiofur sodium as indicated by the above said tables, the potency of Crystalline Ceftiofur sodium is maintained over a long shelf period unlike the amorphous Ceftiofur Sodium.

In one more embodiment of the present invention the Ceftiofur sodium obtained according to the present invention having good stability over conventional Ceftiofur sodium also has less residual solvent over the amorphous sample prepared by prior art.

Crystalline Ceftiofur sodium obtained according to the present invention may be used in the same indications as Ceftiofur sodium provided by a prior art process or Ceftiofur sodium currently on market. Crystalline Ceftiofur sodium according to this invention useful as the active antibiotic drug compound in pharmaceutical dosage forms for treating valuable mammalian animals and humans to treat bacterial infections in that valuable animal or human, and more particularly useful as a veterinary antibiotic drug to treat valuable animals such as cattle, swine, horses, sheep, goats, dogs and cats to fight the effects of bacterial infections caused by susceptible organisms, such as *Pasturella hemolitica, Pasturella multiocida, Salmonella typhimurium, Salmonella choleraeasuis, Actinbacillus plearopneumoniae, Streptococcus suis, Haemophilus somus, E. coli, Staphylococcus aureus* and the like, some of which are commonly associated with diseases in animals, such as bovine respiratory disease and swine respiratory disease.

In another embodiment of the present invention, acylation of FURACA of formula (II) in accordance to step (a) is carried out either by approach 1 or by approach 2 as depicted in scheme (I), by utilizing the conventional processes known in the literature.

Approach 1

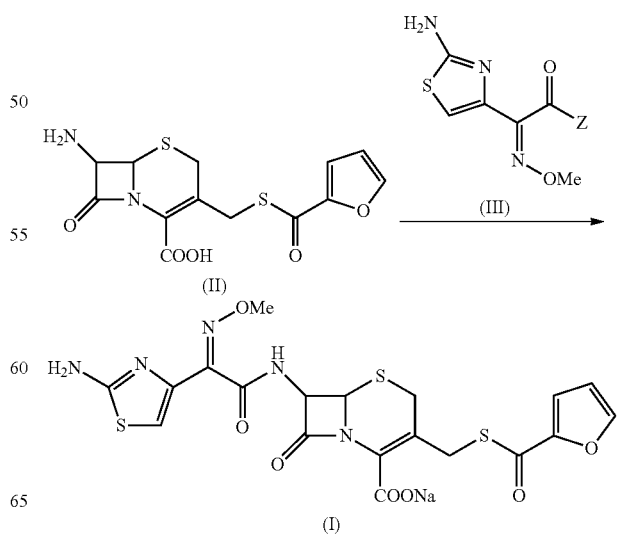

Approach 2

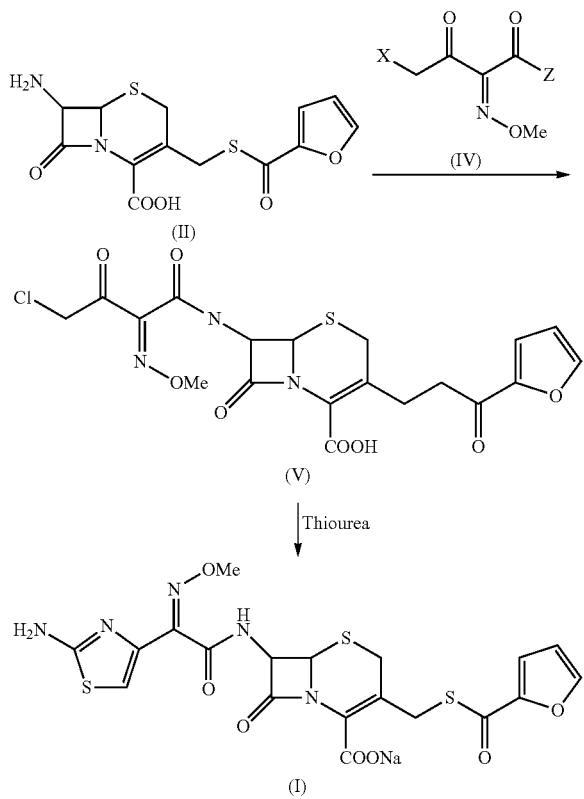

Z is an activactivating group

Approach 1 involves direct acylation with 7-aminothiazole substituent of formula (III) with FURACA of formula (II) yields Ceftiofur of formula (I), and approach two involves acylating the FURACA with compound of formula (IV) followed by cyclizing the ensuing compound of formula (V) with thiourea to yield Ceftiofur of formula (I).

In another embodiment of the present invention of the approach 1 the reaction mass was optionally treated using solvent like ethyl acetate or dichloromethane in order to remove the by-products obtained.

In still another embodiment of the present invention, the Ceftiofur sodium is isolated directly from the reaction mass comprising water miscible organic solvent like THF, acetone, ethyl methyl ketone, diglyme, butanone, dioxane, DMF, acetonitrile, methanol, ethanol, isopropyl alcohol and the like; and water with out using reverse osmosis technique, or solvent precipitation technique, or lyophilization technique or weak salt-strong salt relationship technique. Accordingly the present invention provides a crystallization of Ceftiofur sodium directly from reaction mass which comprises crystallizing Ceftiofur sodium from the reaction mass comprising water, and/or water miscible organic solvent, sodium ion source base, and optionally inorganic salt selected from group consisting of sodium chloride, sodium sulphate, sodium bromide, and the like, and/or reaction impurities with out using techniques like reverse osmosis, or solvent precipitation, or lyophilization or weak salt-strong salt relationship.

In another embodiment of the present invention, the present invention avoids the reverse osmosis techniques like membrane filtration technique, which is essential for conventional processes to removal of inorganic salt like sodium chloride. Accordingly, the present invention also avoids the lyophilization technique.

In still another embodiment of the present invention the present invention avoids the conventional technique of isolating Ceftiofur acid and dissolving the Ceftiofur acid with amine to form amine salt further replacing the amine with sodium by using weak salt—strong salt relationship.

The conventional process of preparing highly pure sodium involves converting Ceftiofur into Ceftiofur hydro halide, and converting Ceftiofur hydrochloride into Ceftiofur sodium either by polyvinyl resin treatment or by treating with silylating agents or using membrane filtration. But according to the present invention the purity of Ceftiofur sodium is achieved by direct isolation, there by avoids the complexity associated with the work up procedure and also conventional process requires more time because of the cumbersome workup associated with it and occupy more reactor space in plant. Hence present invention is not only provides Ceftiofur sodium with good quality but also provides a commercially importance process.

In yet another embodiment of the present invention, the organic solvent from step (b) was optionally removed by distillation or by adding sufficient amount of sodium chloride to reaction mass to form by-phasic layer and separating the water miscible organic layer.

In one more embodiment of the present invention, crystallization of Ceftiofur sodium from the reaction mass contains water miscible organic solvent and water is effected by means of cooling the reaction mass to −5° C. to 15° C. or by the addition of sodium chloride or sodium bromide or sodium sulphate; and crystallization of Ceftiofur sodium from the reaction mass contains water only was effected by the addition of sodium chloride (1 time with respect to Furaca) or sodium bromide (1 time with respect to Furaca) or sodium sulphate.

In another embodiment of the present invention the sodium ion source base employed in step (a) is selected from sodium acetate, sodium bicarbonate, sodium hydroxide, sodium 2-ethyl hexonate, sodium carbonate, sodium lactate, sodium dihydrogen orthophosphate and the like.

In still another embodiment of the present invention the Ceftiofur sodium obtained can be converted into stable sterile Ceftiofur sodium or Ceftiofur HCl.

In yet still another embodiment of the present invention the Ceftiofur HCl can be converted into crystalline Ceftiofur sodium without anion exchange resin.

The starting material of the present invention can be prepared by utilizing the process available in the prior art.

In one more embodiment of the present invention the crystalline Ceftiofur sodium prepared according to the present invention may be administered in any conventional dosage form in any conventional manner, routes of administration and dosage form are exemplified in various prior art related to Ceftiofur and also exemplified in U.S. Pat. No. 4,464,367; U.S. Pat. No. 4,902,683, U.S. Pat. No. 5,079,007, U.S. Pat. No. 5,013,713, and U.S. Pat. No. 5,721,359.

Apart from the conventional formulation that are described the Ceftiofur sodium formulation may also contain chelating agent like ethylene diamine tetraacetic acid (EDTA) or a buffer like sodium citrate along with or with out conventional excipient. The pharmaceutical composition may also contain amorphous Ceftiofur sodium along with crystalline Ceftiofur sodium. Surprisingly, it has been observed that the crystalline Ceftiofur sodium as well as mixture of crystalline Ceftiofur sodium along with amorphous material are non-hygroscopic, whereas conventional amorphous Ceftiofur sodium is highly hygroscopic in nature. Because of the hygroscopic nature, amorphous form is relatively less stable.

Example 1

Preparation of Crystalline Ceftiofur Sodium

To a clear solution of Ceftiofur sodium (5.0 g) in water (100 ml) was added sodium chloride (5 g) at ~30° C. slowly. The resultant suspension was stirred for 1.0 Hr at 10° C. The solid obtained was filtered washed with water and dried to yield crystalline Ceftiofur sodium in pure form. Yield: 2.5 g Purity: 99.79%. Moisture content: 9.84%.

Advantages: None of the prior art suggests the preparation of Ceftiofur sodium as crystalline. All the prior art process provides amorphous Ceftiofur sodium, whereas present invention provides Crystalline Ceftiofur sodium.

Example 2

To a clear solution of Ceftiofur sodium (5.0 g) in water (62.5 ml) was added a solution of sodium chloride (5 g) in water (20 ml) at 10-30° C. slowly. The resultant suspension was stirred for 1.0 Hr at 10-30° C. The solid obtained was filtered, washed with water (2.5 ml) and dried to yield crystalline Ceftiofur sodium in pure form. Yield: 3.0 g; Purity: 99.8%. Moisture content: 9.17%

Example 3

To a clear solution of Ceftiofur sodium (5.0 g) in water (100 ml) were added acetone (1 ml) and sodium chloride (5 g) at 10-30° C. slowly. The resultant suspension was stirred for 1.0 Hr at 10-30° C. The solid formed was filtered, washed with water and dried to yield Ceftiofur sodium in pure form. Yield: 2.6 g Purity: 99.68%. Moisture content: 7.92%

Example 4

To a clear solution of Ceftiofur sodium (5.0 g) in water (100 ml) were added THF (1 ml) and sodium chloride (5 g) at 10-30° C. The resultant suspension was stirred for 1.0 Hr at 10-30° C. The solid obtained was filtered, washed with water and dried to yield Ceftiofur sodium in pure form. Yield: 2.6 g Purity: 99.71%. Moisture content: 8.63

Example 5

To a clear solution of Ceftiofur sodium (5.0 g) in water (100 ml) were added Ethyl acetate (1 ml) and sodium chloride (5 g) at 10-30° C. The resultant suspension was stirred for 1.0 Hr at 10-30° C. The solid formed was filtered, washed with water and dried to yield Ceftiofur sodium in pure form. Yield: 2.55 g Purity: 99.69%.

Example 6

Preparation of Ceftiofur Sodium Crude: (Approach 2; Crystallization of Ceftiofur Sodium Directly from Reaction Mass by Cooling without Using Sodium Chloride)

To a solution of 4-chloro-2-methoxyimino-3-oxobutyric acid (60.67 g) in dichloromethane (400 ml), phosphorus pentachloride (73.49 g) was added at −20 to −10° C. under nitrogen atmosphere. The reaction mass was stirred at −10 to 0° C. and washed with chilled purified water at 0-5° C. The organic layer was separated and added to a silylated solution of FURACA (prepared by treating suspension of FURACA (100 g) in dichloromethane (500 ml) with TMCS (24.52 g) and HMDS (36.4 g)) at −10 to −30° C.). After completion of reaction dichloromethane was distilled out under vacuum at 25-30° C. To the residue, aqueous THF (1000 mL) and thiourea (48 g) were added and stirred by maintaining pH at 4.0-8.0 using sodium bicarbonate at 10-20° C. After completion of the reaction, EDTA (5 g), sodium hydrosulphite (5 g) were added and cooled to 0-5° C. The solid obtained was filtered, washed with THF and dried under vacuum to yield pure title compound (107 g; purity by HPLC 99.28%).

Example 7

Preparation of Ceftiofur Sodium Crude: (Approach 1; Crystallization of Ceftiofur Sodium Directly from Reaction Mass Using Sodium Chloride)

To a cold mixture of THF (400 ml), water (156 ml) and FURACA wet (equivalent to 57.5 g) at 3-5° C. was added MAEM (70 g) followed by triethylamine (19 g). The reaction mixture was stirred at 3-5° C. by maintaining the pH in the range of 7.5-8.0. After completion of the reaction, EDTA (2.5 g) and sodium hydrosulphite (2.5 g) were added. The reaction mixture was washed with ethyl acetate (2×300 ml) at 15-20° C. To the aqueous solution, water (100 ml), THF (250 ml) and sodium acetate (46 g) were added at 15-20° C. To the resultant solution was added sodium chloride (25 g) and cooled to 2-5° C. The solid obtained was filtered, washed with THF and dried under vacuum to yield pure title compound (70 g; purity by HPLC 99.40%).

Example 8

Preparation of Ceftiofur Sodium Crude: (Approach 2; Crystallization of Ceftiofur Sodium Directly from Reaction Mass Using Sodium Chloride)

To the solution of 4-chloro-2-methoxyimino-3-oxobutyric acid (60.67 g) in dichloromethane (400 ml), phosphorus pentachloride (73.49 g) was added at −20 to −10° C. under nitrogen atmosphere. The reaction mass was stirred at −10 to 0° C. and washed with chilled purified water at 0-5° C. The organic layer was separated and added to a silylated solution of FURACA (prepared by treating suspension of FURACA (100 g) in dichloromethane (500 ml) with TMCS (24.52 g) and HMDS (36.4 g) at 10-20° C. and stirred to get clear solution at 25-30° C.) at −20 to −30° C. After completion of reaction dichloromethane was distilled out under vacuum at 25-30° C. To the residue THF (500 ml), DM water (500 ml) and thiourea (48 g) were added and stirred by maintaining pH at 5.0-8.0 using sodium bicarbonate at 18-22° C. To the reaction mixture was added sodium chloride (30 g) and separated aqueous layer. To the aqueous layer sodium chloride was added and stirred. The precipitated solid was filtered and washed with THF. Drying the solid under vacuum afforded pure title compound. (98 g, Purity by HPLC 98.48%).

Example 9

Preparation of Ceftiofur Sodium Crude (Approach 1; Crystallization of Ceftiofur Sodium Directly from Reaction Mass Using Sodium Chloride)

To the cold mixture of THF (400 ml) and water (156 ml) and FURACA wet (equivalent to 57.5 g) at 3-5° C. was added Benzothiazol-2-yl (Z)-2-methoxyimino-2-(2-aminothiazole-4-yl)thioacetate (MAEM) (70 g) followed by sodium bicarbonate by maintaining the pH in the range of 7.5-8.0. After completion of the reaction, EDTA (2.5 g) and sodium hydro sulphite (2.5 g) were added. The reaction mixture was washed with ethyl acetate (2×300 ml) at 15-20° C. To the aqueous solution, water (800 ml) and sodium chloride (50 g) were added at 15-20° C. Cooled to 2-5° C., filtered and washed with THF (200 ml). Dried the solid under vacuum yielded pure title compound (65 g, Purity by HPLC 99.40%).

Advantages of the Present Invention

Obviates the isolation of Ceftiofur free acid.

Obviates the complexity associated with normal workup procedure as described in U.S. Pat. No. 6,458,949 and provides a direct process for the crystallization of Ceftiofur sodium.

Obviates the isolation of conventional process of preparing Ceftiofur amine salt and converting the amine into sodium by the addition of sodium salt of weak acid.

Obviates the complexity associated with normal workup procedure as described in WO 2004/039811 and provides a crystallization of Ceftiofur sodium.

Since the direct isolation or crystallization of Ceftiofur sodium obviates the complexity associated with the workup procedure and in the present invention reaction time is short and hence makes the process commercially important.

Good stability even at elevated temperature.

High purity and non-hygroscopic nature.

Good flow-properties and high bulk density

Example 10

Preparation of Ceftiofur Sodium

To a clear solution of Ceftiofur sodium crude (50.0 g) in water (1000 ml) was added sodium chloride (50 g) at 10-30° C. slowly. The resultant mixture was stirred for 6.0 Hr at 10-30° C. Filtering the solid, washing with water (25 ml) and drying afforded crystalline Ceftiofur sodium in pure form (30 g; purity by HPLC 99.80%). Moisture content: 9.45%

Example 11

Preparation of Ceftiofur Sodium

To a clear solution of Ceftiofur sodium crude (50.0 g) in water (1000 ml) was added sodium sulphate (100 g) at 10-30° C. slowly. The resultant mixture was stirred for 6.0 Hr at 10-30° C. Filtering the solid, washing with water (25 ml) and drying afforded crystalline Ceftiofur sodium in pure form (28 g; purity by HPLC 99.70%).

Example 12

Preparation of Ceftiofur Sodium Sterile

To a suspension of Ceftiofur sodium (15 g) in water (75 ml) was added sodium bicarbonate to adjust the pH to 7.0-8.5. To the resulting mixture was added a solution of potassium dihydrogen orthophosphate (0.36 g) in water (8.6 ml). The pH of the solution was adjusted to 6.5-7.0 using sodium bicarbonate. The resulting solution was filtered through 0.2μ filter and lyophilized to get pure Ceftiofur sodium sterile.

Example 13

Preparation of Ceftiofur Hydrochloride

To a suspension of crystalline Ceftiofur sodium (10 g) in water (30 ml) was added THF (87 ml) at 10-30° C. To that sodium chloride (14 g) was added. pH of the solution was adjusted to 2.5-3.5. Organic layer pH was adjusted to 0.5-1.5 using conc. HCl. Addition of diisopropyl ether followed by filtration yielded pure title compound.]

Example 14

Crystalline Ceftiofur Sodium from Ceftiofur Hydrochloride

To a suspension of ceftiofur hydrochloride (25 g) in water (400 ml) was added sodium bicarbonate till to get clear solution (pH 6.5-8.5). To the clear solution, a solution of sodium chloride (22.5 g) in water (100 ml) was added slowly and the resultant suspension was stirred for 1.0 hr at 10-30° C. The solid obtained was filtered and washed with water (2.5 ml) to yield crystalline Ceftiofur sodium in pure form. Yield 7.5 g; purity 99.74%; Moisture content: 10.08%

Example 15

Preparation of Ceftiofur Sodium Crystalline Buffered with Potassium Dihydrogen Orthophosphate Crystalline Ceftiofur sodium (100 g) was blended with potassium dihydrogen orthophosphate (2.4 g) and sodium bicarbonate till to get uniform pH.

We claim:

1. Crystalline salt of Ceftiofur sodium of formula (I)

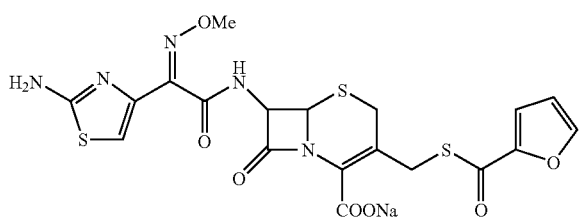

(I)

having X-ray diffraction pattern, which comprises 2θ values (Cu K alpha-1 λ=1.54056 A°) of 9.68, 14.56, 14.74, 17.48, 19.88, 20.58, 21.14, 21.42, 21.92, 22.36, 23.94, 24.16, 25.08, 25.56, 28.30, 28.54, 28.76 (±0.20).

2. A process for the preparation of Ceftiofur sodium of formula (I)

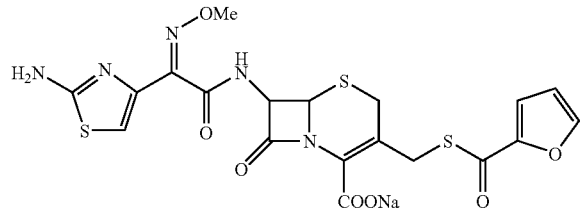

having X-ray diffraction pattern, which comprises 2θ values (Cu K alpha-1 λ=1.54056 A°) of 9.68, 14.56, 14.74, 17.48, 19.88, 20.58, 21.14, 21.42, 21.92, 22.36, 23.94, 24.16, 25.08, 25.56, 28.30, 28.54, 28.76 (±0.20), the process comprising the steps of:
  i) obtaining Ceftiofur sodium in water;
  ii) optionally adding an organic solvent;
  iii) adding alkaline metal salts selected from group comprising of sodium chloride, sodium bicarbonate, sodium sulphate, sodium bromide, potassium dihydrogen orthophospate or mixture thereof; and
  iv) isolating Ceftiofur sodium as crystalline product.

3. A process as claimed in claim 2, wherein the organic solvent used in step (ii) is selected from THF, acetone, ethyl acetate, butyl acetate, ethyl methyl ketone, diglyme, butanone, dioxane or DMF.

4. Physical admixture of crystalline Ceftiofur sodium according to claim 1, with potassium dihydrogen orthophosphate and sodium bicarbonate.

5. A pharmaceutical composition comprising the crystalline Ceftiofur sodium of claim 1 and a buffer.

6. Crystalline Ceftiofur sodium of formula (I) as claimed in claim 1, having the same X-ray diffractogram as set out in FIG. 1.

7. Crystalline Ceftiofur Sodium as claimed in claim 6, having the moisture content in the range of 7.0 to 11%.

8. A pharmaceutical composition comprising a mixture of crystalline Ceftiofur Sodium as claimed in claim 1 with amorphous Ceftiofur sodium.

* * * * *